(12) United States Patent
Taylor

(10) Patent No.: US 6,706,042 B2
(45) Date of Patent: Mar. 16, 2004

(54) TISSUE DISTRACTOR

(75) Inventor: Andrew Clive Taylor, Chichester (GB)

(73) Assignee: Finsbury (Development) Limited, Leatherhead (GB)

(*) Notice: Subject to any disclaimer, the term of this patent is extended or adjusted under 35 U.S.C. 154(b) by 128 days.

(21) Appl. No.: 10/099,298

(22) Filed: Mar. 15, 2002

(65) Prior Publication Data
US 2002/0143344 A1 Oct. 3, 2002

(30) Foreign Application Priority Data
Mar. 16, 2001 (GB) .............................................. 0106588

(51) Int. Cl.[7] .............................................. A61B 17/66
(52) U.S. Cl. ............................................ 606/57; 606/58
(58) Field of Search ............................ 606/57, 54, 53, 606/58, 55, 60, 62, 63, 90, 105

(56) References Cited

U.S. PATENT DOCUMENTS

| | | | | |
|---|---|---|---|---|
| 5,180,380 A | * | 1/1993 | Pursley et al. ................. | 606/54 |
| 5,626,579 A | * | 5/1997 | Muschler et al. .............. | 606/60 |
| 5,626,581 A | * | 5/1997 | Staehlin et al. ................ | 606/63 |
| 5,961,553 A | * | 10/1999 | Coty et al. ..................... | 606/62 |
| 6,022,349 A | * | 2/2000 | McLeod et al. ............... | 606/58 |
| 6,033,412 A | * | 3/2000 | Losken et al. ............... | 606/105 |
| 6,383,185 B1 | * | 5/2002 | Baumgart ..................... | 606/63 |

* cited by examiner

Primary Examiner—Michael J. Milano
Assistant Examiner—Jessica R Baxter
(74) Attorney, Agent, or Firm—Greer, Burns & Crain, Ltd.

(57) ABSTRACT

A mechanism for powering an auto-extensible tissue distractor, e.g. a bone fixator, is described in which a movable device is caused to move in small incremental steps of a few μm each along an elongate member towards its distal end under the influence of one or more piezoelectric actuators.

29 Claims, 9 Drawing Sheets

TISSUE DISTRACTOR

This invention relates to tissue distractors, more particularly to a mechanism for powering an auto-extensible tissue distractor, such as a bone fixator.

Since the turn of the last century when Ilizarov discovered that new bone and soft tissue is regenerated under the effect of slow and gradual distraction, external fixation has been utilised in the treatment of various bone conditions. Limb length differences resulting from congenital, developmental, post-traumatic or post-surgical causes may be treated in this manner. The procedure also lends itself to the treatment of congenital deformities, post-traumatic bone deformities, non-healing fractures and bone loss from tumour, trauma or infection.

Traditionally an external bone fixator has been used which comprises a framework of metal rings connected by rods, whereby each ring is connected to the bone by a plurality of wires under tension or by pins. Titanium pins may be used to support the bone. Presently, a wide variety of designs of fixator are available and are suitable for withstanding the forces imposed by the full weight of the patient.

In surgical limb lengthening, the bone is subjected to osteotomy so as to sever it into two or more parts before the fixator is attached to the severed parts of the bone. In the course of the operation the surgeon will attach at least one pair of pins to each of the severed parts of the bone and then join the pins externally of the patient's limb by means of a rod or rods. Generally there is at least one rod on each side of the limb. Just a few days after surgery the patient is encouraged to resume normal use of the limb in order to maintain joint flexibility and to facilitate muscle growth to match the osteogenesis.

Approximately one week after the surgery to fit the fixator, manual adjustments are commenced in order to lengthen the rods equally so as to separate the severed ends of the bone at a rate of about 1 mm per day. An increase of more than about 1 mm per day results in a slowing of the osteogenesis and an increase of less than about 1 mm per day can result in premature consolidation.

In surgical limb straightening the bone can be severed completely or partially. If the bone is completely severed, then the rod or rods on one side of the limb may be lengthened at a greater rate than the rod or rods on the other side thereof. Alternatively the bone can be partially severed according to a technique known as open wedge osteotomy, in which case a bone fixator may be needed only on the side of the bone in which the cut has been made by the surgeon.

It has further been found that osteogenesis proceeds more satisfactorily if frequent small adjustments in bone length are made by distraction rather than larger less frequent adjustments of bone length. Hence adjustments of about 0.25 mm every 6 hours are recommended. This places a burden upon the patient and carer to conform to a routine which can be very disruptive to day to day life.

It is very common for patients to experience a great deal of pain each time that the fixator is incrementally lengthened. This can make the four times daily lengthening procedure a traumatic experience both for the patient and for the patient's carer, particularly if the patient is a young child. Since the entire bone lengthening or straightening process can last from three to six months this can impose a continuing great strain not only on the patient but also on those caring for the patient. Moreover this procedure tends to lead to very high complication rates so that it is not uncommon for the complication rate to be as high as about 200% which means that each patient on average experiences at least two incidents during a course of bone lengthening or straightening treatment requiring a return to hospital, possibly for further surgery.

Another problem with external bone fixators is that there is a significant risk of infection arising at the site of each pin or wire.

It has been proposed to utilise gradual motorised distraction in which a typical procedure could involve applying a very small incremental lengthening over 1000 times per day which still achieves an average bone lengthening rate of about 1 mm per day.

It would be desirable to provide an auto-extensible tissue distractor, such as a bone fixator, which can effect substantially continuous distraction of bone or other living tissue throughout the day, even while the patient is asleep, thereby avoiding for the patient the pain associated with a several times daily incremental lengthening of the bone or other tissue. It would also be desirable to provide a bone fixator of sufficiently compact size to enable its use as an internal bone fixator, either attached surgically to the outside of the patient's bone or even to the inside the patient's bone, whereby the fixator can remain in situ after the bone lengthening or straightening process has been completed. It would be further desirable to provide a bone fixator which effects continuous bone distraction and which is suitable for external use or for implantation within or adjacent the bone to be lengthened.

The present invention accordingly seeks to provide a mechanism for use with a tissue distractor which enables tissue distraction to be effected substantially continuously throughout the day and night during the entire tissue distraction process. It further seeks to provide a mechanism for powering an auto-extensible bone fixator. It also seeks to provide such a mechanism which can be used with an external fixator. Another objective of the invention is to provide a mechanism for powering an auto-extensible internal tissue distractor. In addition the invention seeks to provide an auto-extensible bone fixator which avoids for the patient the pain associated with a four times daily incremental lengthening of about 0.25 mm by effecting substantially continuous bone distraction throughout the patient's waking hours (and possibly also during the patient's sleeping hours). A further objective of the invention is to provide a mechanism for powering a tissue distractor, such as a bone fixator, so as to cause it to extend in a series of very small increments so as to avoid, for a patient fitted with the tissue distractor, the experience of pain associated due to the extension of the tissue distractor. Yet another objective of the invention is to provide a compact bone fixator which can be used as an internal bone fixator, for example by being attached surgically to the outside of the patient's bone or by being implanted inside the patient's bone. In addition the invention seeks to provide a compact design of bone fixator which effects substantially continuous bone distraction and which is suitable for external use or for implantation within or adjacent a bone to be surgically lengthened or straightened. An additional objective is to provide an auto-extensible mechanism for a bone fixator which can automatically lengthen at an essentially continuous and controllable rate while measuring both the rate of lengthening and also the load being imposed on the bone being lengthened and its associated soft tissue.

According to the present invention there is provided a mechanism for powering an auto-extensible tissue distractor comprising:

an elongate member having a proximal end, a distal end, and a longitudinal axis;

at least one movable device movably mounted on the elongate member for movement therealong in a direction away from the proximal end towards the distal end, said movable device comprising:
- a first crawler portion operatively engaged with the elongate member and having a first non-return means for preventing movement of the first crawler portion at least in a direction towards the proximal end;
- a second crawler portion operatively engaged with the elongate member and disposed nearer the distal end than the first crawler portion, the second crawler portion having a second non-return means for preventing movement of the second crawler portion at least in a direction towards the proximal end;
- piezoelectric drive means adapted to undergo elongation by a discrete incremental amount in an elongation direction upon application of a selected voltage potential thereto and at a rate of elongation dependent upon the rate of increase of the voltage applied thereto, the piezoelectric drive means being operatively mounted between the first and second crawler portions with its elongation direction aligned substantially parallel to the longitudinal axis of the elongate member so that, upon applying the selected voltage potential thereto at a predetermined rate of increase of applied voltage with the first non-return means preventing the first crawler portion from moving in a direction towards the proximal end of the elongate member and with the second non-return means permitting movement of the second crawler portion towards the distal end, the second crawler portion is caused to move at a predetermined rate of elongation a distance corresponding to the incremental amount towards the distal end, and so that, upon removal of the selected voltage from the piezoelectric means with the second non-return means preventing the second crawler portion from moving towards the proximal end and with the first non-return means permitting the first crawler portion to move towards the distal end, the piezoelectric drive means reverts to its original length and thereby moves the first crawler portion a distance along the elongate member towards the distal end corresponding to the incremental amount;

voltage generating means for applying a voltage potential to the piezoelectric means; and control means for repeatedly applying the selected voltage potential at the predetermined rate of increase of applied voltage to the piezoelectric means to cause the movable device to move in incremental steps along the elongate member in a controlled manner.

Throughout this specification and claims the terms "increase" and "increasing", when used in relation to voltage potentials, refer to the magnitude of the voltage and do not necessarily imply, for example, that the voltage potential is increasing from 0 to +1000 v but also include within their meanings the case where the voltage potential is decreasing from 0 to −1000 v, for example.

In a preferred form of mechanism according to the invention the movable device includes a rigid outer tubular member surrounding the first crawler portion, the second crawler portion, and the piezoelectric means. Moreover the piezoelectric means may be interposed between the first crawler portion and the second crawler portion for causing separation of the first crawler portion and the second crawler portion longitudinally of the elongate member.

In such a mechanism the first crawler portion may include a first substantially frustoconical recess whose axis is substantially coaxial with the longitudinal axis of the elongate member, and the first non-return means may comprise a spring loaded collet arranged to seat in the first substantially frustoconical recess to exert a braking action on the first crawler portion, the mechanism further comprising a first supplementary piezoelectric means for moving the collet away from the first substantially frustoconical recess to release the braking action of the first non-return means. Typically the first supplementary piezoelectric means comprises a tubular piezoelectric actuator. Alternatively the first supplementary piezoelectric means may comprise a pair of rod-like piezoelectric actuators. In addition the second crawler portion may include a second substantially frustoconical recess whose axis is substantially coaxial with the longitudinal axis of the elongate member, while the second non-return means comprises a spring loaded collet arranged to seat in the second substantially frustoconical recess to exert a braking action on the second crawler portion, the mechanism further comprising a second supplementary piezoelectric means for moving the collet away from the second substantially frustoconical recess to release the braking action of the second non-return means. Such a second supplementary piezoelectric means may comprise a tubular piezoelectric actuator or a pair of rod-like piezoelectric actuators.

In such a mechanism the piezoelectric means may be tubular.

In an alternative preferred embodiment the first non-return means and the second non-return means each comprise sprags which brake movement towards the proximal end of the elongate member and which permit movement only in a direction towards the distal end of the elongate member. In such a mechanism the second crawler portion may be held captive on the first crawler portion and be spring biased away therefrom, while the piezoelectric means comprises a pair of rod-like piezoelectric actuators.

In yet another preferred form of mechanism according to the invention the second crawler portion is held captive on the first crawler portion and is spring biased away therefrom, and the piezoelectric means comprises a tubular piezoelectric actuator surrounding the elongate member. In such a mechanism the first crawler portion may comprise a collar having a pair of free ends, the collar being arranged to grip the elongate rod to brake movement of the first crawler portion relative to the elongate rod, and brake release means comprising a transversely mounted piezoelectric means arranged to separate the free ends of the collar to release the braking action thereof on the elongate member. In this case the second crawler portion may comprise a collar having a pair of free ends, the collar being arranged to grip the elongate rod to brake movement of the second crawler portion relative to the elongate rod, and brake release means comprising a transversely mounted piezoelectric means arranged to separate the free ends of the collar to release the braking action thereof on the elongate member.

In a still further form of mechanism according to the invention the elongate member comprises a tubular portion, the first crawler portion comprises a first plug slidably disposed within the tubular portion and connected to an outer ring member which surrounds the elongate member, the second crawler portion comprises a second plug slidably disposed within the tubular portion and connected to a main body portion surrounding the elongate member, the first non-return means and the second non-return means each comprise respective sprags, the piezoelectric drive means is disposed within the tubular portion between the first and second plugs, and spring biassing means are provided between the first crawler portion and the second crawler portion and arranged to undergo loading while the first non-return means prevents movement of the first crawler portion during movement of the second crawler portion and for the loading to be released while the second non-return means prevents movement of the second crawler portion so as to cause the first crawler portion to move towards the distal end of the elongate member.

In the mechanism of the invention the control means may include a load sensor, such as a load cell, for measuring the load applied by or to the piezoelectric drive means. Such a load cell may comprise a piezoelectric crystal upon which the piezoelectric drive means is arranged to impinge.

In a preferred form of the invention the control means includes a microprocessor, amplifier means operatively connected to the piezoelectric drive means and under the control of the microprocessor for applying at least one voltage potential signal to the piezoelectric drive means at a selected rate of increase thereof for causing the movable device to move in incremental steps along the elongate member in a controlled manner, feedback amplifier means connected to the load sensor and arranged to receive a feedback signal therefrom, the feedback amplifier means being operatively connected to the microprocessor for supplying thereto a feedback signal in dependence on the load sensed by the load sensor and the microprocessor being arranged to receive the feedback signal from the feedback amplifier means and to adjust the rate of increase of the at least one voltage potential signal so as to ensure that the load exerted by or on the piezoelectric drive means and sensed by the load sensor does not exceed a predetermined value. Preferably the microprocessor is arranged to store data indicative of the at least one voltage potential signal, of time, and of the feedback signal from the feedback amplifier means. Typically the at least one voltage potential signal comprises a d.c. voltage potential signal which is typically in the range of from about 100 v to about 1000 v. However, if desired, the at least one voltage potential signal may comprise an oscillatory signal having a frequency of from about 5 Hz to about 2 kHz, e.g. about 1 kHz, having an amplitude of from about 1 $\mu$m to about 10 $\mu$m imposed upon the d.c. voltage potential signal. In this last mentioned case the amplitude of the oscillatory signal must not exceed the overall extension of the piezoelectric drive means caused by the d.c. voltage potential at the time so as not to damage the piezoelectric drive means. The oscillatory signal can be superimposed on the d.c. voltage potential signal either while the magnitude of the voltage potential is increasing or while the d.c. voltage potential is held substantially constant either before or after the piezoelectric drive means has reached its maximum extension during an incremental step.

It will normally be preferred for the microprocessor to be connected to an input/output device by means of which set point values can be input into the microprocessor from an external input device and data stored in the microprocessor can be downloaded to an external source. Such set point values can, for example, include set point values indicative of at least one of the following items:

(i) the rate of increase of d.c. voltage potential with time applied to the piezoelectric drive means thereby to determine the rate of extension thereof;

(ii) a functional relationship involving the rate of increase of the d.c. voltage potential applied to the piezoelectric drive means and also the load sensed by the load cell;

(iii) the maximum d.c. voltage potential to be applied to the piezoelectric drive means thereby to determine the size of each said incremental step;

(iv) the maximum load sensed by the load sensor permitted to be applied by or to the piezoelectric drive means thereby to determine the load imposed on the bone callus and associated soft tissue;

(iv) the maximum time period during which the movable device is permitted to move thereby to determine the maximum distance through which the movable device is permitted to move along the elongate member;

(v) the maximum distance through which the movable device is permitted to move along the elongate member.

Desirably the mechanism is arranged so that the incremental steps range from about 5 $\mu$m to about 120 $\mu$m, preferably about 10 $\mu$m to about 120 $\mu$m, for example, from about 40 $\mu$m to about 80 $\mu$m.

The mechanism will typically be adjusted so that the control means causes the movable device to move along the movable member at a rate of about 1 mm per day.

The invention also extends to an auto-extensible tissue distractor, such as a bone fixator, fitted with a mechanism of the above described type.

In order that the invention may be clearly understood and readily carried into effect some preferred embodiments thereof will now be described, by way of example only, with reference to the accompanying drawings, wherein.

Figure 1:
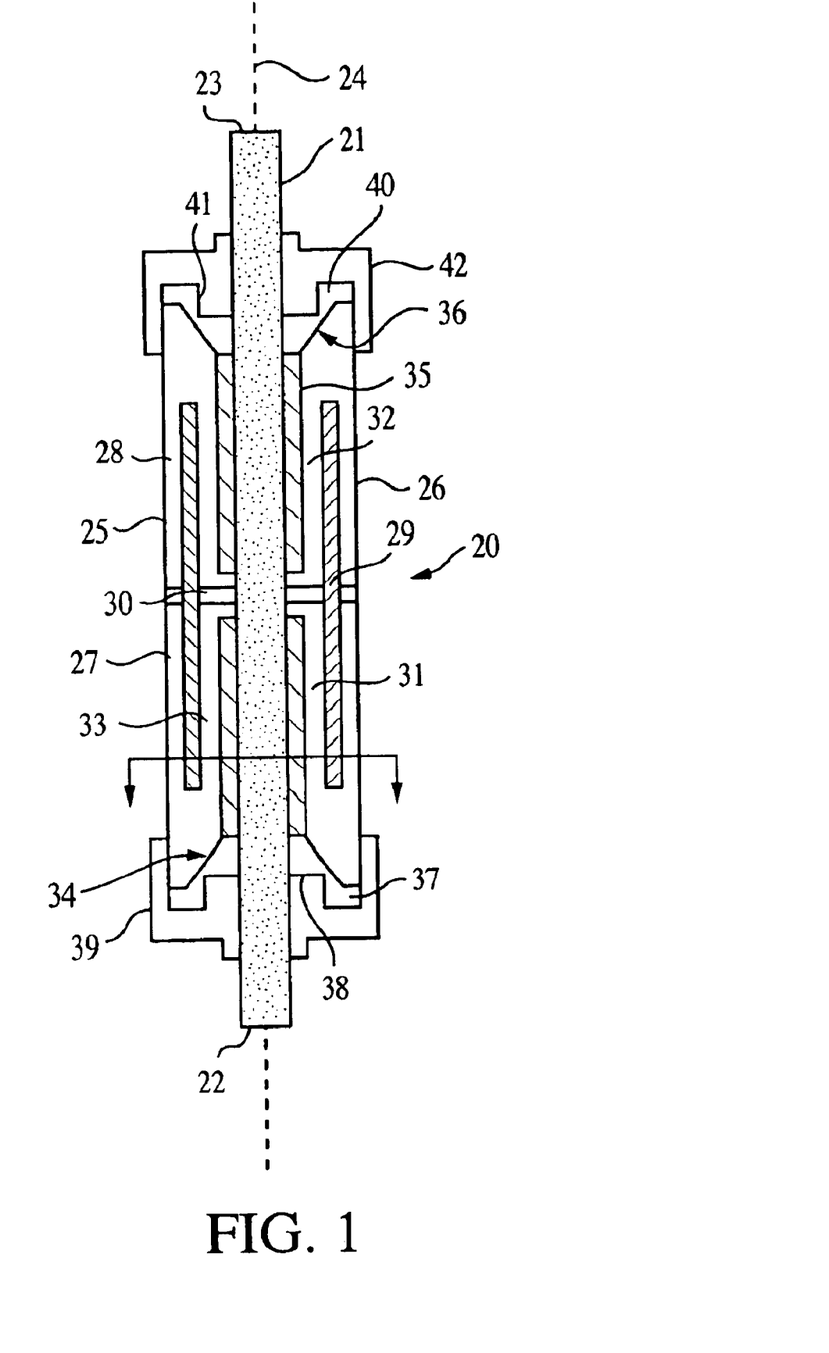
FIG. 1 is a longitudinal section of a first form of mechanism for powering an auto-extensible bone fixator constructed in accordance with the invention.

Referring to FIG. 1 of the drawings, a mechanism 20 for powering an auto-extensible bone fixator comprises an elongate member 21, only part of which is shown, having a proximal end 22 and a distal end 23, and a longitudinal axis 24. Mounted on elongate member 21 is a movable device 25 which comprises a cylindrical outer housing 26 and inserts 27 and 28. Received within inserts 27 and 28 is an outer cylindrical piezoelectric actuator 29 comprising a stack of toroidal piezoelectric crystals. A typical material for the piezoelectric crystals is lead zirconate titanate. The individual piezoelectric crystals are not shown but each is sandwiched between a respective pair of electrodes to which an electric potential can be applied. Moreover each piezoelectric crystal is insulated from its neighbours. Upon application of an electric potential of from about 100 volts to about 1000 volts across each of the crystals of actuator 29, the entire stack extends by a small amount, e.g. up to about 120 μm, in a direction parallel to the longitudinal axis 24 of elongate member 21. In doing so it exerts a force of up to 3000 Newtons.

Between inserts 27 and 28 there is a clearance gap 30 which separates a first crawler portion 31 from a second crawler portion 32. Around elongate member 22 there is a second piezoelectric actuator 33 which forms part of a first non-return means 34 which is intended to lock the first crawler portion 31 to the elongate member 22 and prevent movement thereof at least towards the proximal end 22 of elongate member 21. As in the case of piezoelectric actuator 29, second piezoelectric actuator 33 comprises a stack of toroidal piezoelectric crystals each sandwiched between a pair of electrodes and each insulated from any neighbouring piezoelectric crystal of the stack so that, upon application of an electric potential thereacross, the length of the stack extends by a small distance, for example, 50 μm in a direction parallel to the longitudinal axis 22 of elongate member 21.

At the other end of the movable device 26 there is a third piezoelectric actuator 35, similar to piezoelectric actuator 33, which forms part of a second non-return means 36 which is intended to lock second crawler portion 32 to elongate member 21 so as to prevent movement thereof at least in a direction towards the proximal end 22 of elongate member 21.

First non-return means 34 further includes a collet 37 which is biased towards the distal end 23 of elongate member 21 by means of a diaphragm spring 38 which forms part of an end cap 39 attached to the proximal end of the housing 26.

Second non-return means 36 also includes a collet 40 which is biased towards the proximal end 22 of elongate member 21 by means of a diaphragm spring 41 which forms part of an end cap 42 secured to the distal end 23 of housing 26.

In use of a bone fixator fitted with mechanism 20, the surgeon attaches to a proximal end portion of elongate member 21 by means of suitable clamps and rings (not shown) a pair of pins attached to one of the severed ends of the bone to be lengthened or straightened and attaches to the movable device 25 by means of further clamps and rings (not shown) a similar pair of pins fixed to the other severed end of the bone to be lengthened or straightened.

In the absence of a voltage signal to any of piezoelectric actuators 29, 33 and 35, movable device 25 is locked to elongate member 21 under the action of the two non-return means 34 and 36, the diaphragm springs 38 and 41 forcing the respective collets 37 and 40 into engagement with the ends of rubber insert 30 and preventing movement of movable device along elongate member 21 in either direction.

Upon supplying a voltage potential to piezoelectric actuator 35, this undergoes extension and lifts collet 40 against the spring action of diaphragm 41, through a small distance, e.g. 50 μm, which is sufficient to release the braking action of non-return means 36 which has been preventing movement of second crawler portion 32 towards the distal end 23 of elongate member 21. While still applying a voltage potential to piezoelectric actuator 35, a voltage potential is then applied to piezoelectric actuator 29. As a result of the ensuing extension of piezoelectric actuator 29, second crawler portion 32 is moved a corresponding distance towards the distal end 23 of elongate member 21, thereby extending the bone to be lengthened or straightened by a corresponding amount.

While still applying the voltage potential to piezoelectric actuator 29, the voltage potential applied to piezoelectric actuator 35 is then switched off, causing this to revert to its original length. Under the influence of diaphragm spring 41, collet 40 returns to a locking position thus again providing a braking action upon second crawler portion 32.

A voltage potential is then applied to piezoelectric actuator 33, thereby causing it to extend a predetermined amount. In so doing, it pushes collet 37 towards the proximal end 22 of elongate member 21 against the action of diaphragm spring 38 and releases the locking action of non-return means 34 preventing movement of first crawler portion 31 relative to elongate member 21. Next the voltage potential applied to piezoelectric actuator 29 is reduced to zero, thereby causing this to revert to its original length. In so doing it will cause first crawler portion 30 to move a corresponding distance towards the distal end 23 of elongate member 21.

The whole procedure can then be repeated, possibly after a predetermined interval, so as to cause bone fixator 20 to extend by an "inchworm" technique in a series of cycles, each involving movement of movable device 25 in incremental steps along elongate member 21, and thereby provide substantially continuous lengthening of bone fixator 20 throughout the patient's waking hours (and possibly also during his or her sleeping hours) at a rate of about 1 mm per day, without causing significant pain levels to the patient.

If desired, a low amplitude oscillatory signal, for example, having a frequency of from about 5 Hz to about 2 kHz can be superimposed on the voltage potentials applied to the piezoelectric actuators 29, 33, and 35, with a view to providing enhancement to the process of osteogenesis.

Figure 2:
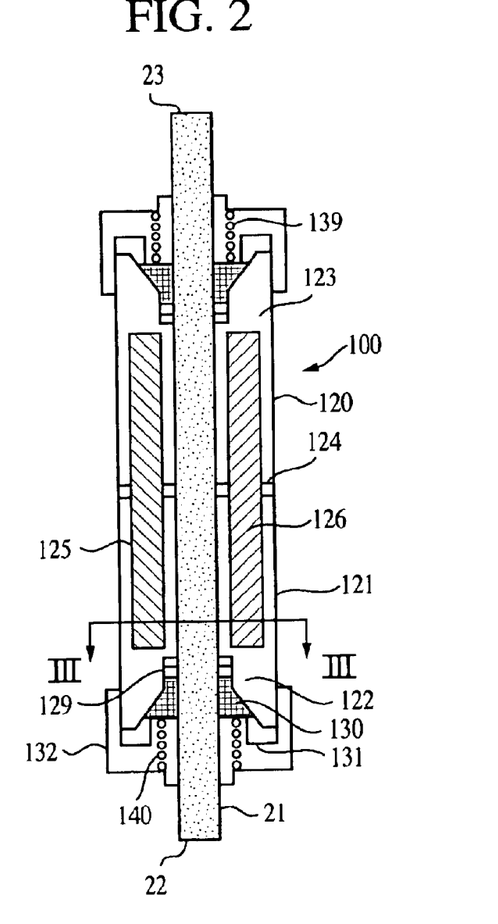
FIG. 2 is a longitudinal section through part of a second form of mechanism for powering an auto-extensible bone fixator according to the invention.
Figure 3:
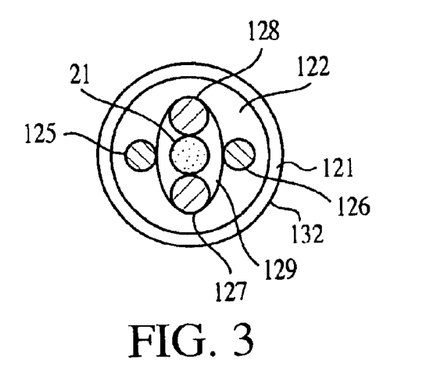
FIG. 3 is a cross section on the line III—III of FIG. 2.
Figure 4:
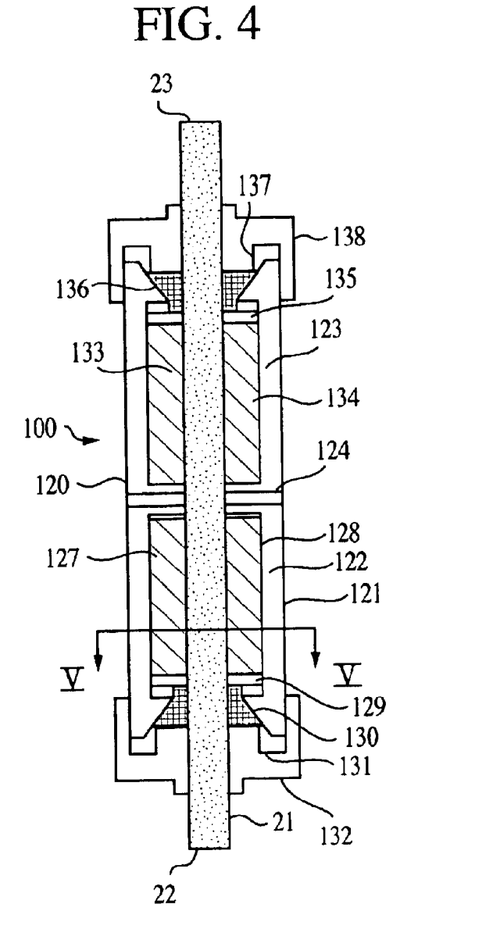
FIG. 4 is a side view in section through the mechanism of FIGS. 2 and 3.
Figure 5:
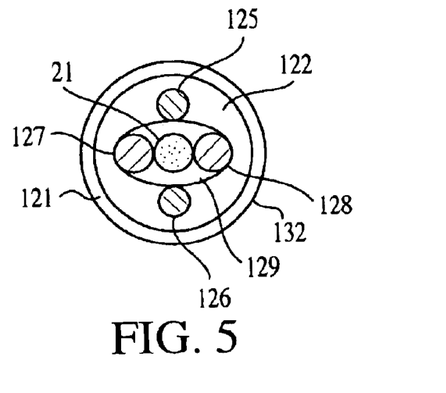
FIG. 5 is a cross section on the line V—V of FIG. 4.

The mechanism 20 of FIG. 1 has three piezoelectric actuators 29, 33, and 35. FIGS. 2 to 5 illustrate a second form of mechanism 100 for powering an auto-extensible bone fixator with six piezoelectric actuators. As illustrated in FIG. 2 mechanism 100 includes an elongate member 21 and a movable device 120 which has an outer cylindrical casing 121, a first insert 122 forming a first crawler portion and a second insert 123 forming a second crawler portion. First crawler portion 122 is separated from second crawler portion 123 by a clearance gap 124.

Instead of having a cylindrical tubular piezoelectric actuator 28 as in mechanism 20 of FIG. 1, mechanism 100 has two rod-like piezoelectric actuators 125 and 126. Moreover in place of tubular piezoelectric actuator 32 of FIG. 1, mechanism 100 has two rod-like piezoelectric actuators 127 and 128. Adjacent piezoelectric actuators 127 and 128 there is a pusher plate 129 which bears upon collet 130. Collet 130 is urged towards distal end 23 of elongate member 21 by means of a diaphragm spring 131 which forms part of an end cap 132.

In addition, tubular piezoelectric actuator 34 of fixator 20 of FIG. 1 is replaced by a pair of rod-like piezoelectric actuators 133 and 134 which bear on a pusher plate 135 (which is similar to pusher plate 129). Pusher plate 135 in turn bears against collet 136 which is biased towards the proximal end 22 of elongate member 21 by a diaphragm spring 137 that forms part of end cap 138.

Figure 6:
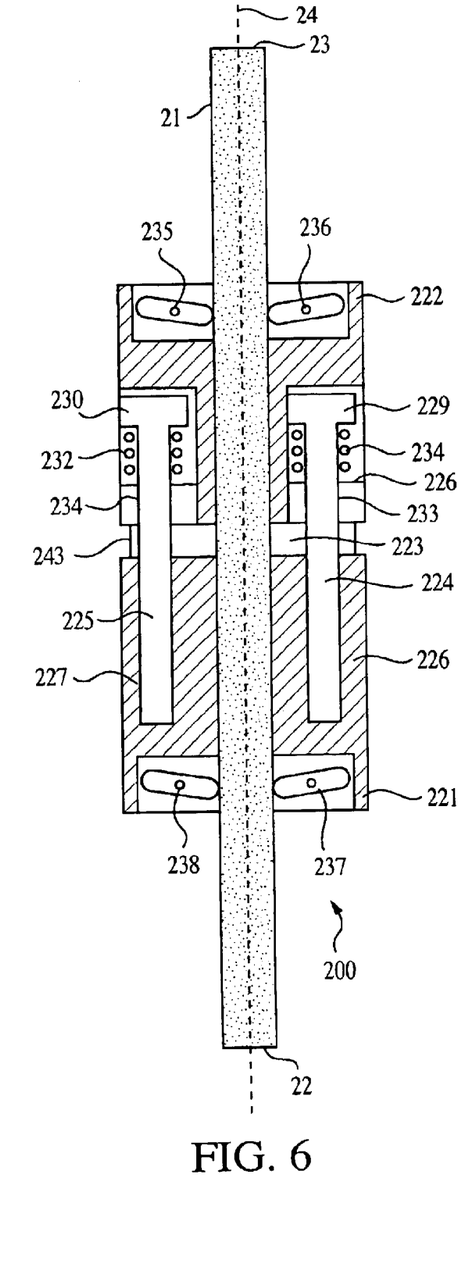
FIG. 6 is a longitudinal section through a third form of mechanism for powering a bone fixator constructed in accordance with the invention.
Figure 7:
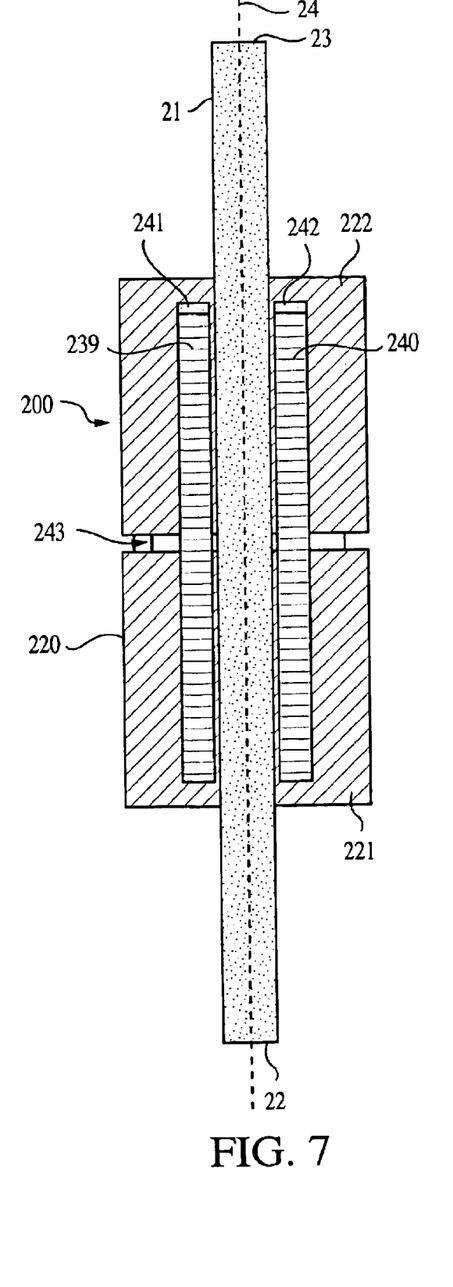
FIG. 7 is a side view, also in section, of the mechanism of FIG. 6.

FIGS. 6 and 7 illustrate a third form of mechanism 200 for powering an auto-extensible bone fixator which incorporates a pair of piezoelectric actuators, rather than the three piezoelectric actuators 28, 32, and 24 of mechanism 20 of FIG. 1 or the three pairs of piezoelectric actuators of mechanism 100 of FIGS. 2 to 5.

Mechanism 200 includes a movable device 220 which is shown mounted on elongate member 21. It comprises a first crawler portion 221 and a second crawler portion 222 made, for example, of stainless steel with a clearance gap 223 between them. A pair of bolts 224 and 225 are threadedly engaged in respective threaded bores 226 and 227 in first crawler portion 221. Bolts 224 and 225 pass through a plate 228 on second crawler portion 222 and their respective heads 229 and 230 are biased away from plate 228 by compression springs 231 and 232. The shafts of bolts 224 and 225 pass through smooth bores 233 and 234 in plate 228. By this arrangement second crawler portion 222 is biased away from first crawler portion 221 in a direction towards distal end 23 of elongate member 21 but is retained captive with respect thereto.

First crawler portion 221 is further provided with a pair of sprags 235 and 236 which permit movable device 220 to move along elongate member 21 in a direction towards distal end 23 but not in the opposite direction. Sprays 235 and 236 thus act as a uni-directional lock. Similar sprags 237 and 238 are provided on second crawler portion 222 and permit movable device 220 to move along elongate member 21 towards distal end 23 but not in the opposite direction. Sprags 237 also act as a uni-directional lock.

Movable device 220 also incorporates a pair of rod-like piezoelectric actuators 239 and 240 which, like the piezoelectric actuators of the embodiments of FIG. 1 and of FIGS. 2 to 5, are each formed of a stack of piezoelectric crystals, each of which is interposed between a pair of electrodes by means of which a voltage potential can be simultaneously applied across the individual piezoelectric crystals to cause the stack 239 or 240 to lengthen by a predetermined amount, e.g. about 60 $\mu$m with a force of up to about 3000 Newtons.

Reference numerals 241 and 242 indicate load sensors, while reference numeral 243 indicates a silicon rubber diaphragm seal to prevent ingress of contaminants.

Upon applying a voltage potential across the piezoelectric actuators 239 and 240, these are caused to lengthen. Sprags 237 and 238 act as non-return devices to prevent first crawler portion 221 from moving towards the proximal end 22 of elongate member 21 but sprags 235 and 236 allow second crawler portion 222 to move towards distal end 23. Upon removal of the voltage potential across piezoelectric actuators 239 and 240, these revert to their original length. Sprags 235 and 236 then act as a non-return device to prevent second crawler portion 222 from moving towards proximal end 22 of elongate member 21 but sprags 237 and 237 allow first crawler portion 221 to move towards the distal end 23 of elongate member 21. Upon repeating the procedure movable device 220 is again moved a small distance along elongate member 21 towards its distal end. Hence if one end of the severed bone to be lengthened or straightened is attached by means of a pair of pins and suitable clamps (not shown) to movable device 220 and the other end of the severed bone is similarly attached to a proximal end portion of elongate member 21, effectively continuous distraction of the bone can be achieved. By varying the rate of increase of voltage potential applied to the piezoelectric crystals and/or the rest intervals between incremental movements of the crawler portions 221 and 222, the speed of distraction can be selectively altered.

Figure 8:
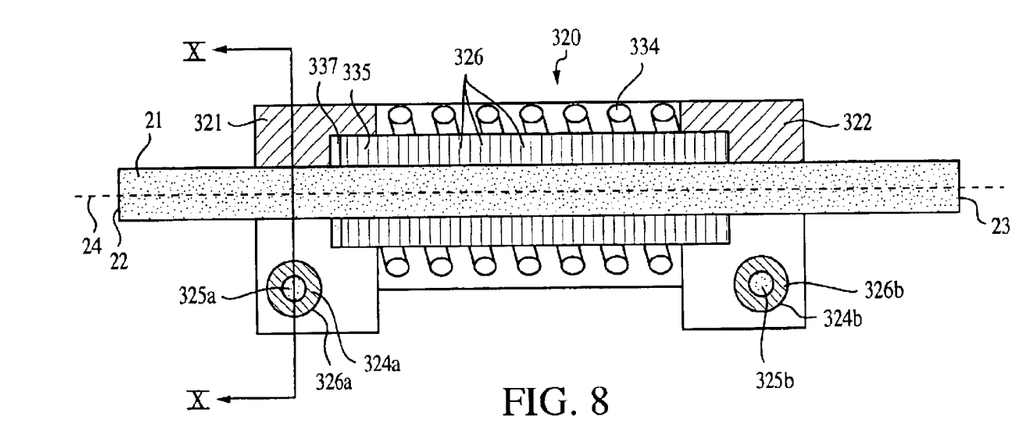
FIG. 8 is a longitudinal section through a fourth form of mechanism for powering an auto-extensible bone fixator constructed in accordance with the teachings of the invention.

FIG. 8 illustrates a mechanism 300 for powering an auto-extensible bone fixator which includes a movable device 320 mounted on an elongate member 21. It comprises a first crawler portion 321, which is typically made of stainless steel, and a second crawler portion 322 which is a mirror image of first crawler portion 321. First crawler portion 321 is in the form of a clamp member which surrounds elongate member 21 except for a small gap 323 (see FIGS. 9 and 10) and normally grips elongate member 21. As can be seen from FIG. 10, first crawler portion 321 is formed with a transverse bore 324 which receives a waisted rod 325 with threaded ends and a first tubular piezoelectric actuator 326 made up of a plurality of piezoelectric crystal slices 327 each positioned between a pair of electrodes (not shown) across which can be applied a voltage potential to cause piezoelectric actuator 326a to lengthen by a predetermined small amount. The ends of rod 325a carry nuts 328a and 329a which bear against end caps 330a and 331a which are screwed on first crawler portion 321. Waisted rod 325a acts like a spring to close the gap between portions 332a and 333a. When no voltage potential is applied across the piezoelectric crystal slices 327, first crawler portion 321 grips and is locked on elongate member 21 under the spring action of waisted rod 325a and thus acts as a brake to prevent movement of first crawler portion 321 in either direction along elongate member 21. However, upon applying a voltage potential across the piezoelectric actuator 326a, actuator 326a is caused to lengthen by a predetermined amount and bears on end caps 330a and 331a thereby stretching waisted rod 325a and allowing corners 332a and 333a to separate so as to widen gap 323a. As a result of gap 323a widening, first crawler portion 321 is caused to release its grip on elongate member 21 and permit first crawler member 321 to move along elongate member 21. Second crawler portion 322 is similar in construction to first crawler portion 321 and like parts are designated by like reference numerals but with substitution of the suffix "b" in place of the suffix "a". It operates in a similar manner to first crawler portion 321.

Between first crawler portion 321 and second crawler portion 322 there is a tension spring 334. First crawler portion 321 is connected to second crawler portion 322 by means of a tubular piezoelectric actuator 335 consisting of a plurality of toroidal slices 336 of piezoelectric crystal, each disposed between a pair of electrodes across which can be applied a voltage potential to cause actuator 335 to lengthen by a small amount, e.g. about 120 $\mu$m.

Reference numeral 337 indicates a load cell for monitoring the load applied by piezoelectric actuator 335.

In use of a bone fixator fitted with mechanism 300 the surgeon affixes one severed end of the bone to be lengthened or straightened to a proximal end portion of elongate member 21, using conventional pins, rings, and clamps (not shown), and attaches the other severed end of the bone, again using conventional pins, rings and clamps, to the movable device 320. A voltage potential is applied to piezoelectric actuator 326b of second crawler portion 322 to permit the gap 323b therein to expand. In this way the brake action of second crawler portion 322 is temporarily removed, thus permitting second crawler portion 322 to move along elongate member 21. At this time no voltage potential is applied to the piezoelectric actuator 326a of first crawler portion 321 which accordingly remains locked on elongate member 21 due to the brake action thereof. Next a voltage potential is gradually applied to piezoelectric actuator 335 causing it to lengthen by a predetermined amount and thereby move second crawler portion 222 towards the distal end 23 at a rate corresponding to the rate of increase of applied voltage. Next the voltage potential applied to piezoelectric actuator 326b of second crawler portion 322 is reduced to zero, causing that actuator 326b to return to its original length and gap 323b to close due to the resilient properties of second crawler portion 322 and thereby cause second crawler portion 322 to again grip elongate member 21 and provide a braking action preventing its movement in either direction along elongate member 21.

Thereupon a voltage potential is applied to the piezoelectric actuator 326a of first crawler portion 321 causing it to lengthen by about 60 μm and to permit the corresponding gap 323a to widen by a similar amount. In this way the braking action of first crawler portion 321 is overcome so that first crawler portion 321 is now free to move along elongate member 21. Upon subsequently switching off the voltage potential applied to piezoelectric actuator 335, this again returns to its original length and tension spring 334 then draws first crawler portion 321 a corresponding distance along elongate member 21 towards its distal end 23. Next the voltage potential applied to piezoelectric actuator 326a of first crawler portion 321 is switched off, allowing it to return to its original length and permitting gap 323 of first crawler portion 321 to close and re-brake first crawler portion 321 by clamping it on elongate member 21.

This procedure can then be repeated immediately or after a suitable time interval so as to move movable device 320 in "inchworm" fashion further along elongate member 21 towards its distal end 23. In this way bone distraction can be effected in a substantially continuous manner throughout the patient's waking and sleeping hours without requiring attention from a carer and without causing significant pain to the patient. The rate of bone distraction can alternatively be adjusted by varying the rate of voltage potential increase applied to piezoelectric actuator 335.

Figure 11:
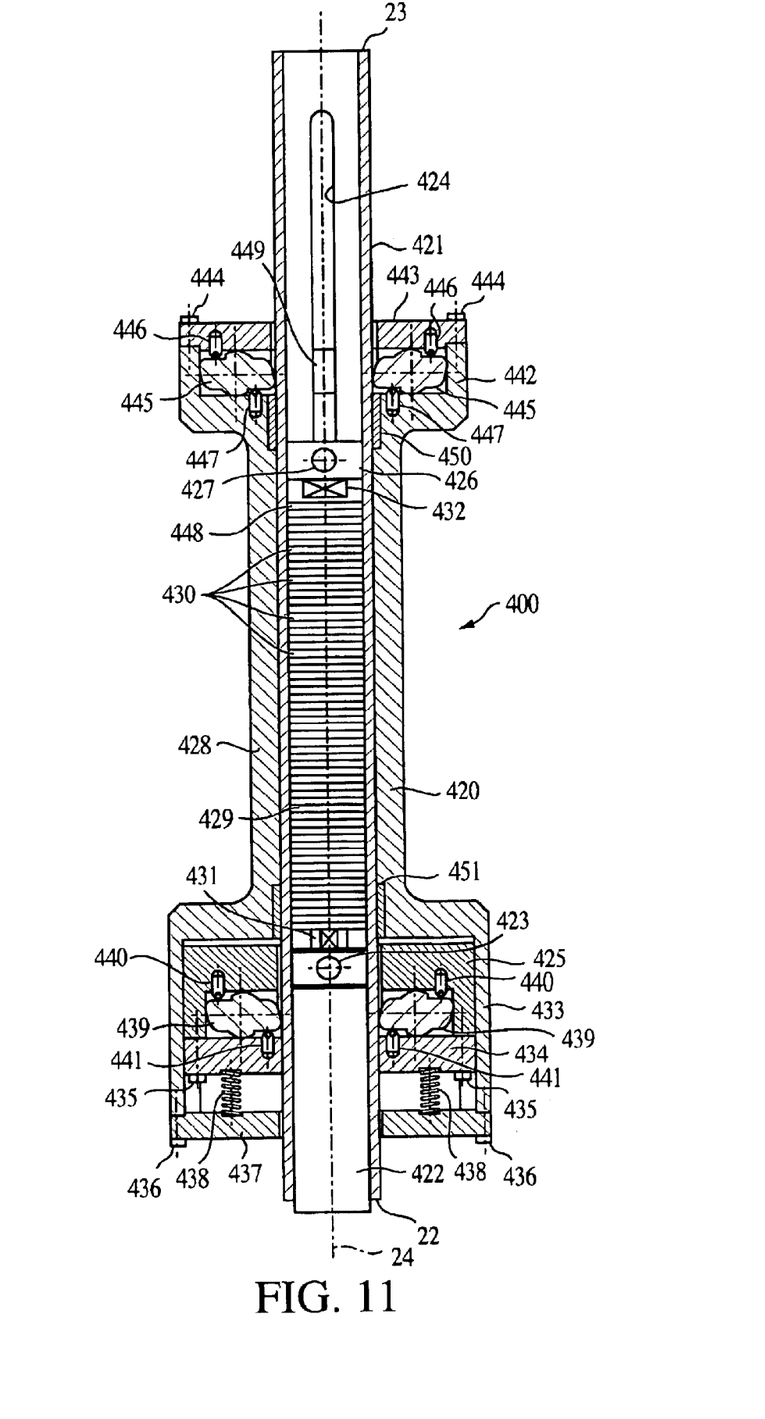
FIG. 11 is a longitudinal section through a further form of mechanism for powering an auto-extensible bone fixator according to the invention.

FIG. 11 illustrates a still further form of mechanism 400 for powering an auto-extensible bone fixator. This comprises a movable device 420 slidably mounted on a tubular elongate member 421. In FIG. 11 tubular elongate member 421 is shown as being relatively short. Its proximal end is indicated by reference numeral 22 and its distal end by reference numeral 23. However, member 421 can be of any convenient length depending, for example, upon the length of the bone to be lengthened or straightened A plug 422 is slidably located within tubular elongate member 421 and is affixed, by means of a transverse shear pin or bolt 423, whose shaft can slide in a pair of diametrically opposed slots 424 in tubular elongate member 421, to an outer ring member 425. Only one slot 424 is depicted in FIG. 11 and only one end thereof is visible. However, the slots 424 extend at least as far as the position depicted of transverse shear pin or bolt 423.

Towards the other end of slots 424 a second smaller plug 426 is also slidably mounted within tubular elongate member 421 and can move independently from plug 422. Plug 426 is secured by means of a second transverse shear pin or bolt 427 to the main body 428 of movable device 420. The shaft of shear pin or bolt 427 can also slide in slots 424.

Between plugs 422 and 426 there is positioned a piezoelectric actuator 429 of the type sold by Physikcomponente, details of which are available on the internet at www.physikcomponente.com. Such a piezoelectric actuator is described by its distributor as a PZT ceramic stack protected by an internally spring preload stainless steel case. (The abbreviation "PZT" means lead zirconate titanate). In FIG. 11 the stainless steel case is not shown. However, FIG. 11 indicates a stack of piezoelectric crystals 430, each sandwiched between a pair of electrodes (not shown) with the electrodes of each crystal 430 electrically insulated from those of neighbouring crystals 430. Actuator 429 has a male threaded end 431 by means of which it is secured in a corresponding bore in plug 422 and a female threaded end 432 in which is engaged a corresponding male threaded spigot (not shown) on plug 426.

Outer ring member 425 is bell shaped and is itself received within a bell shaped end portion 433 of the main body 428. The open end of the bell shaped outer ring member 425 is closed by means of an annular end member 434 which is held in place by screws 435.

Screws 436 secure an annular end closure 437 to bell shaped end portion 433 to close off the open end of the main body 428. Springs 438 bias end closure 434 and hence outer ring member 425 away from end closure member 437. Within outer ring member 425 there are mounted a number of sprags 439, only two of which are shown in FIG. 11, which are symmetrically disposed around the longitudinal axis of movable device 420. There may be, for example, eight such sprags 439. Spring loaded ball bearings 440 and 441 bear against sprags 439.

The other end of main body 428 is also formed as a second bell shaped portion 442 whose open end is closed by means of a further annular member 443 which is held in place by screws 444. A second set of sprags 445 is mounted in the cavity in bell shaped end portion 442. Spring loaded ball bearings 446 and 447 bear against sprags 445.

As will be appreciated by the skilled reader, sprags 439 and 445 will allow movement of movable device 420 along the tubular elongate member 421, but in one direction only, i.e. in the upward direction as depicted in FIG. 11. Movement of movable device 420 in the opposite direction, i.e. downwardly as depicted in FIG. 11, is prevented by sprags 439 and 445.

Reference numeral 448 indicates a load cell, in the form of a piezoelectric crystal which is incorporated in piezoelectric actuator 429, by means of which the load being applied to or exerted on the piezoelectric actuator 429 can be monitored. A tongue 449 which projects into slot 424 from second bell shaped portion 442 prevents rotation of the movable device 420 about the axis 24 of the elongate member 23. Bearings 450 and 451 are provided between movable device 420 and elongate member 421.

In operation of movable device 400, application of a voltage across the piezoelectric crystals 430 of piezoelectric actuator 429 will cause it to extend in length by, for example, up to 120 μm, e.g. about 40 μm, at a rate determined by the rate of increase of the applied voltage potential. Sprags 439 will not allow outer ring member 425 to move downwardly (as drawn in FIG. 11) but sprags 445 will allow main body 428 to move upwardly (as shown in FIG. 11). Hence main body 428 will move upwardly and compress springs 438 because outer ring member 425 will remain stationary.

Upon removal of the voltage, piezoelectric actuator 429 will revert to its original length. Sprags 445 will now prevent main body 428 from moving downwardly (as drawn in FIG. 11) but sprags 439 will now allow outer ring member 425 to move upwardly (as drawn) under the influence of springs 438.

Upon re-applying a voltage across the crystals 430 of piezoelectric actuator 429 the movable member 420 can be caused to move an additional increment up (as drawn) tubular elongate member 421.

If main body 420 is connected by conventional pins (not shown) to one end of the bone being lengthened or straightened and tubular elongate member 421 also by conventional pins (not shown) to the other end thereof, mechanism 400 can be used to lengthen or straighten a patient's bone.

Figure 9:
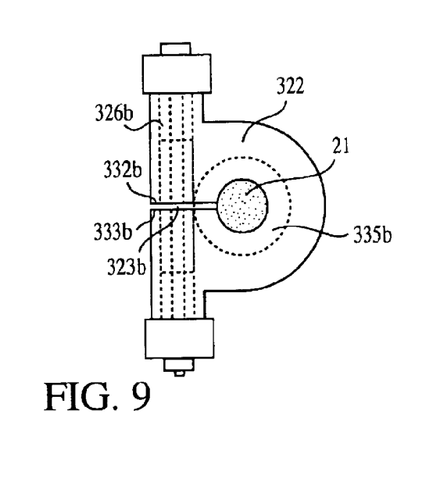
FIG. 9 is an end view of the mechanism of FIG. 8.
Figure 10:
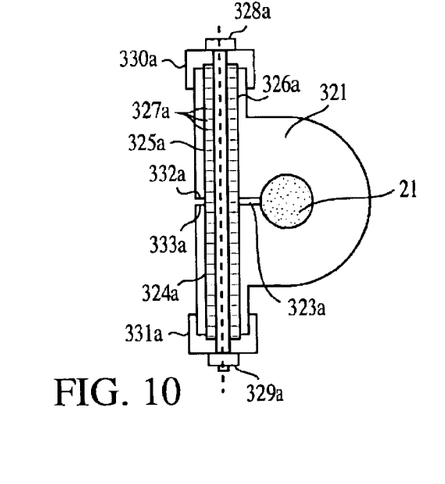
FIG. 10 is a cross section on the line X—X of FIG. 8.
Figure 12:
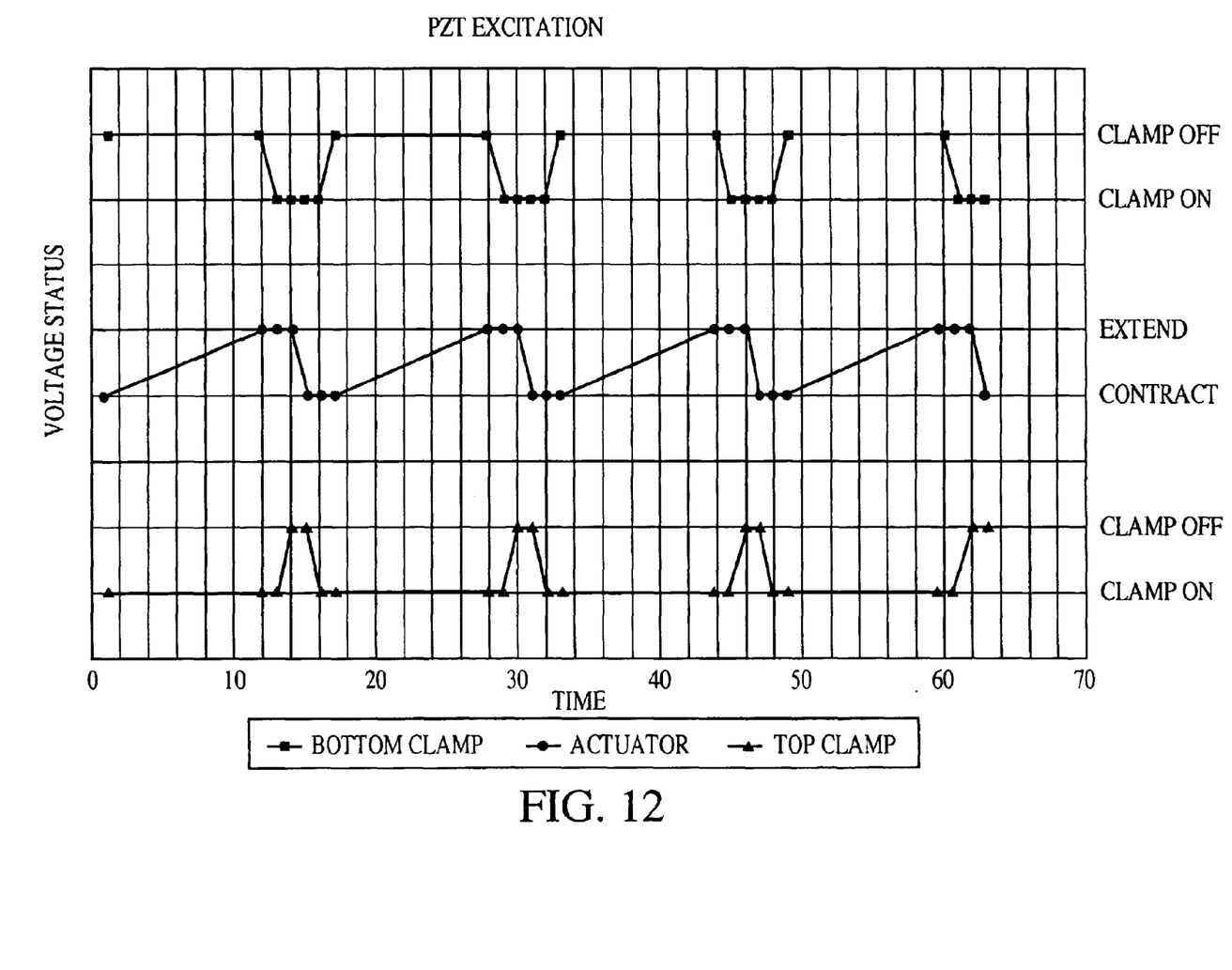
FIG. 12 includes time-voltage graphs illustrating operation of the mechanism of FIGS. 8 to 10.

FIG. 12 illustrates a sequence of operations for the movable device 320 of FIGS. 8 to 10. In FIG. 12 the "bottom clamp" is piezoelectric actuator 326a, while the "top clamp" is the other piezoelectric actuator 326b and the "actuator" is the piezoelectric actuator 335. The time scale is measured in arbitrary units. The status of the "bottom" piezoelectric actuator 326a is shown by the lowermost graph of FIG. 12, that of piezoelectric actuator 335 by the middle graph, and that of the "upper" piezoelectric actuator 326b by the uppermost graph.

At time zero a voltage is applied across the crystals of piezoelectric actuator 326b to cause it to extend and stretch waisted rod 325b thereby to release the clamping action of second crawler portion 322 on elongate member 21. This is indicated in FIG. 12 by the designation "CLAMP OFF" against the top graph. No voltage is applied to piezoelectric actuator 326a so that crawler portion 321 remains clamped to elongate member 21. This is indicated by the designation "CLAMP ON" against the lowermost graph of FIG. 12.

An increasing d.c. voltage potential is applied to piezoelectric actuator 335, causing this to extend and move second crawler portion 322 along elongate member 321 towards its distal end 23 at a rate dependent upon the rate of increase (or ramping rate) of the d.c. voltage potential applied to piezoelectric actuator 335, as indicated on the middle graph of FIG. 12 (which is labelled "EXTEND" and "CONTRACT"). When the voltage potential applied to piezoelectric actuator 335 reaches a predetermined peak voltage, e.g. 1000 V, it is maintained at this value for a short time, during which time the voltage potential applied to piezoelectric actuator 326b is reduced to zero. As a result piezoelectric actuator 326b and waisted rod 325b revert to their original lengths and the clamping action of second crawler portion 322 is resumed. This is indicated by the designation "CLAMP OFF" against the uppermost graph of FIG. 12. Next, while still applying the peak d.c. potential to piezoelectric actuator 335, a corresponding voltage potential is applied to piezoelectric actuator 326a which causes both it and waisted rod 325a to extend and thereby release the clamping action of first crawler portion 321 on elongate member 21, as indicated by the designation "CLAMP OFF" against the lowermost graph of FIG. 12. Then, to complete the cycle, the voltage potential applied to piezoelectric actuator 335 is reduced to zero causing it to revert to its original length and allowing tension spring 334 to draw first crawler portion 221 along elongate member 21 towards its distal end 23.

This procedure is then repeated to cause movable device to move slowly along elongate member 21 in "inchworm" fashion.

Preferably the extension caused by the application of the selected voltage potential to piezoelectric actuator 335 and the number of cycles per day for which this procedure is repeated are selected so as to give a rate of movement of the movable device 320 along elongate member 21 which is about 1 mm per day.

Variations within each cycle are possible. For example, instead of choosing a rate of increase of the voltage potential applied to piezoelectric actuator 335 so that the voltage potential steadily increases over most of the cycle, as illustrated in FIG. 12, and allowing only a short interval between succeeding cycles, it is alternatively possible to utilise a somewhat faster rate of increase of the voltage potential applied to piezoelectric actuator 335 but over only a part of each cycle, e.g. about 50% of each cycle until the desired peak voltage potential is attained. In this case the peak voltage potential can be maintained at a substantially constant value over a substantial part of the remainder of each cycle.

If desired, an oscillatory signal can be applied at some point during the cycle so long as the amplitude of the high frequency signal is less than the extension already caused by the voltage potential at the time that the oscillatory signal is applied. Conveniently the oscillatory signal is applied after the full extension has been achieved in the course of the cycle. However, it can be applied before the full extension has been achieved, if desired. Such an oscillatory signal can be, for example, a frequency, typically a sine wave frequency, of about 5 Hz to about 1 kHz, having an amplitude of not more than about 10 μm and is preferably applied after the peak extension caused by the voltage potential has been achieved, for example, after the extension of piezoelectric actuator 335 has reached about 40 μm out of its maximum permissible extension of about 120 μm. At all events, in order not to cause damage to the piezoelectric actuator 335, the amplitude of any oscillatory signal must not exceed the extension caused by the d.c. voltage potential on which the oscillatory signal is superimposed. In this case the piezoelectric actuator 335 does not undergo any further overall extension during the second part of the cycle, although it may be subjected to an oscillatory oscillation of small amplitude. The operation of the piezoelectric actuators 326a and 326b remain as indicated in FIG. 12.

It is of course not necessary always to apply the maximum possible safe operating voltage potential to the piezoelectric actuators, such as piezoelectric actuator 335. Thus, for example, even if the maximum permissible extension achievable by a piezoelectric actuator is about 120 μm, the designer of the tissue distractor, or the orthopaedic surgeon supervising its use, may decide that the movable device shall move in each cycle only, for example, about 40 μm. This has the advantage that lower peak voltage potentials can be used, thus reducing the risk of the external insulation of the movable device breaking down and allowing the patient to suffer electric shocks. For example, the surgeon may decide that application of 25 cycles per day each of about 40 μm will provide the desired distraction rate of approximately 1 mm per day, even though the maximum safe permissible extension of the piezoelectric actuator may be about 120 μm.

Figure 13:
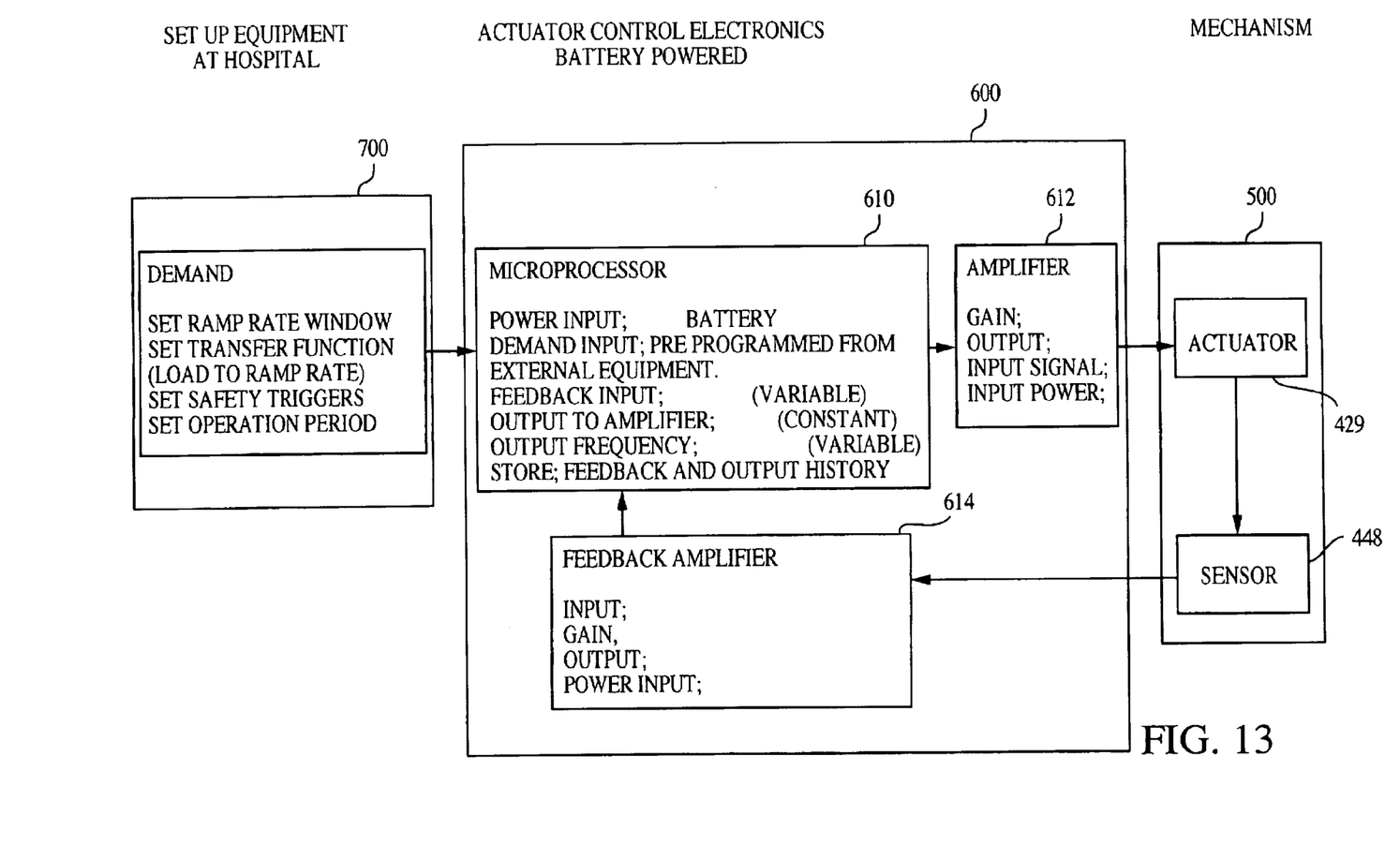
FIG. 13 is a block diagram illustrating operation of the mechanism of FIG. 11.

FIG. 13 is a block diagram indicating how the mechanism 400 of FIG. 11 is used in post-operative treatment of a patient with a limb that needs to be lengthened or straightened by means of a bone fixator 500 which incorporates a movable device of the type illustrated in FIG. 11. Fixator 500 can be attached to the outside of the patient's limb as an external fixator or can be surgically implanted adjacent the patient's bone or inside the patient's bone.

Bone fixator 500 is connected to a battery powered control device 600 which, in the case of an external fixator, is worn by the patient or, in the case of an internal fixator, is surgically implanted under the patient's skin in a similar manner to a heart pacemaker to facilitate its removal when the bone lengthening or straightening has been successfully accomplished. The surgeon in this case may decide either to remove the internal fixator, if this has been positioned adjacent the patient's bone or to leave it in place, particularly if the bone fixator has been installed within the bone.

Control device 600 includes a microprocessor 610, an amplifier 612, and a feedback amplifier 614 which is arranged to receive an input signal from load cell 448. It also includes a battery (not shown) and possibly also a solar cell or an inductive link for recharging the battery.

At the hospital or clinic, or at the surgeon's consulting rooms, the parameters required for controlling the rate of extension of fixator 500 are input into the microprocessor 610 from an input device 700, such as a personal computer.

Such parameters include the rate of ramping the voltage applied to the piezoelectric actuator 429. (The ramping rate is indicated in FIG. 12 by the sloping lines of the middle graph labelled "EXPAND" and "CONTRACT"). The parameters may also include a transfer function (for example, the ratio between the load exerted on the bone or other tissue undergoing distraction as detected by load cell 448 and the voltage ramping rate), as well as safety trigger values to prevent actuator 429 from overloading the bone or other tissue being distracted. The parameter may also include the operation period over which the distraction procedure, e.g. the bone lengthening or straightening procedure, is to be carried out. The surgeon can periodically monitor the patient's progress during periodic consultations and can use input device 700 to vary the parameters input to microprocessor 610. By separating the input device from the control device 600 the risk of the patient accidentally altering the intended operation of the bone fixator 500 is avoided.

Microprocessor 610 receives a power input from the battery. Based upon the parameters input by the surgeon from input device 700 and upon feedback signals from feedback amplifier 614, microprocessor 610 generates appropriate signals to amplifier 612 at an appropriate frequency to cause bone fixator 500 to extend at a favourable rate. Microprocessor 610 also stores information from feedback amplifier 614 and records the history of the output signals to amplifier 612.

Piezoelectric actuator 429 responds to the voltage signals from amplifier 612 and extends at a controlled rate in response to the appropriate instructions input into microprocessor 610 from input device 700 of about 1 mm per day. Load cell 448 acts as a sensor to monitor the load applied to the fixator 500 by the piezoelectric actuator 429. If this inadvertently applies an excessive load, then this is signalled via feedback amplifier 614 to the microprocessor 610 which then reduces the load, for example, by reducing the voltage ramping rate.

Figure 14:
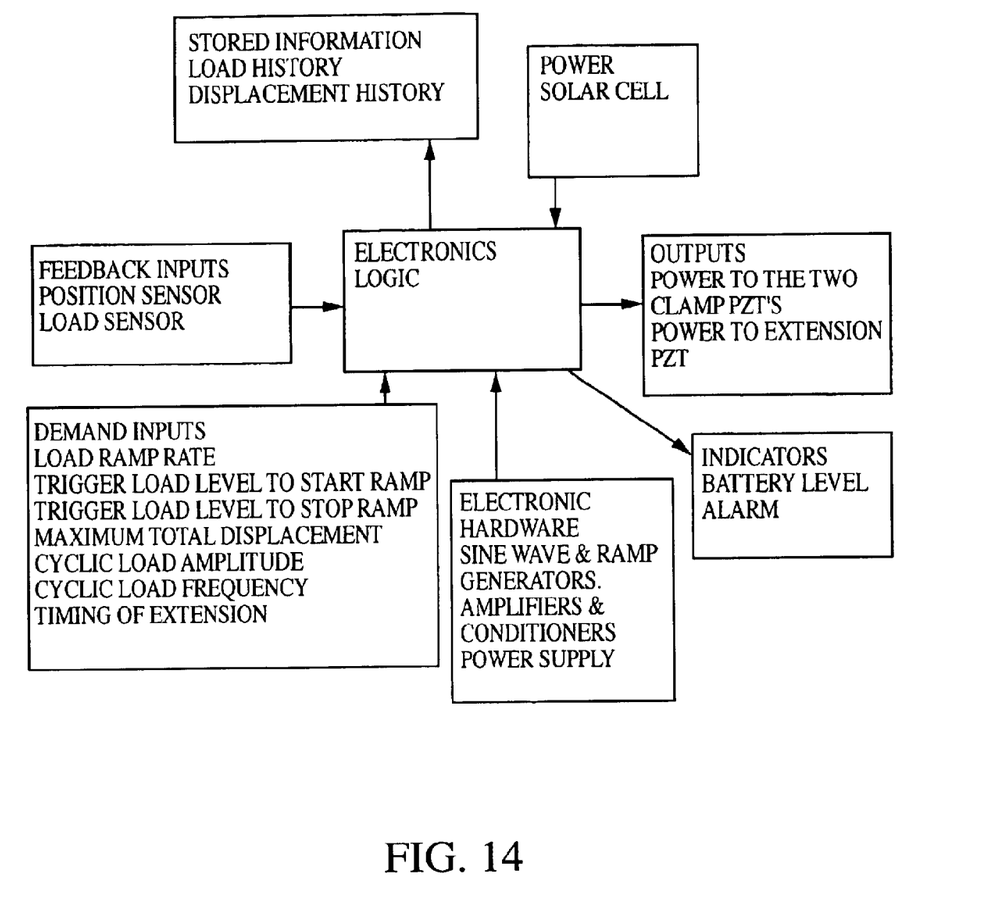
FIG. 14 is a further block diagram illustrating a method of control of the mechanism of FIGS. 8 to 10.

FIG. 14 is a block diagram showing how it is possible to control the movable device 300 of FIGS. 8 to 10. (In FIG. 14 the abbreviation "PZT" indicates a lead zirconate titanate piezoelectric actuator).

Figure 15:
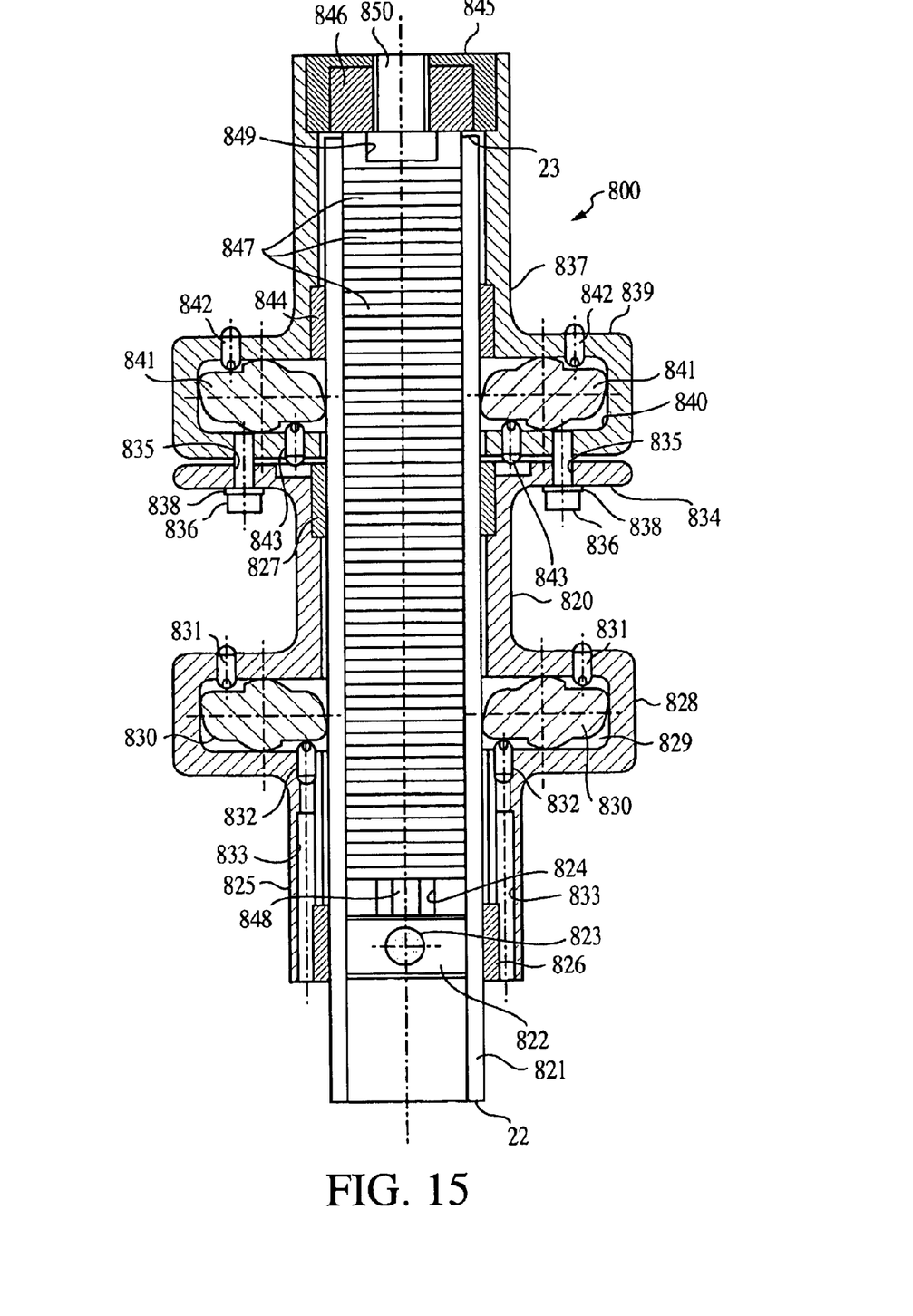
FIG. 15 is a longitudinal section through a still further embodiment of the invention.

FIG. 15 shows a further form of mechanism 800 for powering an auto-extensible bone fixator. This comprises a movable device 820 slidably mounted on a tubular elongate member 821. In FIG. 15 tubular elongate member 821 is shown as being relatively short. Its proximal end is indicated by reference numeral 22 and its distal end by reference numeral 23. However, as with elongate member 421 of the embodiment of FIG. 11, member 821 can be of any convenient length depending, for example, upon the length of the bone to be lengthened or straightened A plug 822 is slidably located within tubular elongate member 821 and is affixed, by means of a transverse shear pin or bolt 823, whose shaft can slide in a slot 824 in tubular elongate member 821, to a first annular crawler portion 825 which surrounds tubular elongate member 821. This carries a bearing 826 at its proximal end and a bearing 827 at its distal end. Shear pin or bolt 823 passes through bearing 826, one of its ends being received in the body of first crawler portion 825.

First crawler portion 825 has an enlarged portion 828 with a hollow interior 829 in which are positioned a plurality of sprags 830, only two of which are shown in FIG. 15, which are symmetrically disposed around the longitudinal axis of movable device 820. There may be, for example, eight such sprags 830. Spring loaded ball bearings 831 and 832 bear against sprags 830. A bore 833 provides access to the adjustment screw of each spring loaded ball bearing 832.

At its distal end first crawler portion 825 is formed with an annular flange 834 which is provided with bores 835 for bolts 836. Bolts 836 pass through bores 835 and are slidably journalled therein, as well as being threadedly engaged in second crawler portion 837. Spring loaded washers 838 bias first crawler portion 825 and second crawler portion 837 towards each other.

Second crawler portion 837 also has an enlarged portion 839 with a hollow interior 840. Sprags 841 are positioned within hollow interior 840. There may be, for example, eight sprags 841, each under the influence of spring loaded ball bearings 842 and 843.

A bearing 844 is positioned adjacent the distal end of enlarged portion 839.

The distal end of second crawler portion 837 is closed by a threaded plug 845 which houses a load cell 846.

Between load cell 846 and plug 822 there is a piezoelectric actuator comprising a stack of piezoelectric crystals 847, each sandwiched between a pair of electrodes (not shown) with the electrodes of each crystal 847 electrically insulated from those of neighbouring crystals 847. Crystals 847 are contained within an internally spring preload stainless steel case (not shown). The piezoelectric actuator has a male threaded end 848 by means of which it is secured in a corresponding bore in plug 822 and a female threaded end 849 in which is engaged a corresponding male threaded spigot 850 mounted in plug 845.

As will be appreciated by the skilled reader, sprags 830 and 841 will allow movement of movable device 820 along the tubular elongate member 821, but in one direction only (i.e. in the upward direction as depicted in FIG. 15), that is to say in the distal direction of elongate member 821. Movement of movable device 820 in the opposite direction, i.e. downwardly as depicted in FIG. 15 towards the proximal end 22 of elongate member 821, is prevented by sprags 830 and 841.

In operation of movable device 800, application of a voltage across the piezoelectric crystals 847 of the piezoelectric actuator will cause it to expand in length by, for example, up to 120 μm, e.g. about 40 μm, at a rate determined by the rate of increase of the applied voltage potential. Sprags 830 will not allow first crawler portion 825 to move downwardly (as drawn in FIG. 15) towards the proximal end 22 of elongate member 821 but sprags 841 will allow second crawler portion 837 to move upwardly (as shown in FIG. 15) in the distal direction of elongate member 821. Hence second crawler portion 837 will move upwardly and compress spring washers 838.

Upon removal of the voltage potential, the piezoelectric actuator will revert to its original length. Sprags 841 will now prevent second crawler portion 837 from moving downwardly (as drawn in FIG. 15) but sprags 841 will now allow first crawler portion 825 to move upwardly (as drawn) under the influence of spring washers 838.

Upon re-applying a voltage potential across the crystals 847 of the piezoelectric actuator, the movable member 820 can be caused to move an additional increment up (as drawn) tubular elongate member 821 towards its distal end 23.

If one or other of first crawler portion 825 and second crawler portion 837 is connected by conventional pins (not shown) and/or a ring to one end of the bone being lengthened or straightened and if tubular elongate member 421 is secured also by conventional pins (not shown) and/or a ring to the other end thereof, mechanism 800 can be used to lengthen or straighten a patient's bone.

Although each of the illustrated mechanisms has been shown with a single movable device on the elongate member, it will be appreciated by those skilled in the art that it would be possible to utilise a fixator comprising an elongate member with two movable devices and to affix one of the surgically severed ends of the bone to be straightened or lengthened each to a respective one of the movable devices. In this case one of the ends of the elongate member would be the proximal end for one of the movable devices but the distal end for the other movable device, while the other end of the elongate member would be the distal end for the first mentioned movable device but the proximal end for the second mentioned movable device.

Tissue distractors in accordance with the invention may also find other uses in surgery. For example, in cases in which the shape of the spine requires to be corrected, tissue distractors may be fitted one on each side of the patient's spinal column, each being connected to at least two vertebrae. By then extending one distractor at a greater rate than it can be attempted to remedy malformations and misalignments of the spinal column. Other usages which can be envisaged for tissue distractors in accordance with the invention include cosmetic surgery, for example for changing the shape of a patient's nose, cheek bone, or lower jaw. Other uses of a tissue distractor in accordance with the invention will be readily apparent to those skilled in the art.

What is claimed is:

1. A mechanism for powering an auto-extensible tissue distractor comprising:

an elongate member having a proximal end, a distal end, and a longitudinal axis;

at least one movable device movably mounted on the elongate member for movement therealong in a direction away from the proximal end towards the distal end, said movable device comprising:

a first crawler portion operatively engaged with the elongate member and having a first non-return means for preventing movement of the first crawler portion at least in a direction towards the proximal end;

a second crawler portion operatively engaged with the elongate member and disposed nearer the distal end than the first crawler portion, the second crawler portion having a second non-return means for preventing movement of the second crawler portion at least in a direction towards the proximal end;

piezoelectric drive means adapted to undergo elongation by a discrete incremental amount in an elongation direction upon application of a selected voltage potential thereto and at a rate of elongation dependent upon the rate of increase of the voltage applied thereto, the piezoelectric drive means being operatively mounted between the first and second crawler portions with its elongation direction aligned substantially parallel to the longitudinal axis of the elongate member so that, upon applying the selected voltage potential thereto at a predetermined rate of increase of applied voltage with the first non-return means preventing the first crawler portion from moving in a direction towards the proximal end of the elongate member and with the second non-return means permitting movement of the second crawler portion towards the distal end, the piezoelectric drive means undergoes elongation and the second crawler portion is caused to move at a predetermined rate of elongation a distance corresponding to the incremental amount towards the distal end, and so that, upon removal of the selected voltage from the piezoelectric means with the second non-return means preventing the second crawler portion from moving towards the proximal end and with the first non-return means permitting the first crawler portion to move towards the distal end, the piezoelectric drive means reverts to its original length and thereby moves the first crawler portion a distance along the elongate member towards the distal end corresponding to the incremental amount;

voltage generating means for applying a voltage potential to the piezoelectric means; and control means for repeatedly applying the selected voltage potential at the predetermined rate of increase of applied voltage to the piezoelectric means to cause the movable device to move in incremental steps along the elongate member in a controlled manner.

2. A mechanism according to claim 1, in which the movable device includes a rigid outer tubular member surrounding the first crawler portion, the second crawler portion, and the piezoelectric means.

3. A mechanism according to claim 2, in which the piezoelectric means is interposed between the first crawler portion and the second crawler portion for causing separation of the first crawler portion and the second crawler portion longitudinally of the elongate member.

4. A mechanism according to claim 2, in which the first crawler portion includes a first substantially frustoconical recess whose axis is substantially coaxial with the longitudinal axis of the elongate member, and in which the first non-return means comprises a spring loaded collet arranged to seat in the first substantially frustoconical recess to exert a braking action on the first crawler portion, the mechanism further comprising a first supplementary piezoelectric means for moving the collet away from the first substantially frustoconical recess to release the braking action of the first non-return means.

5. A mechanism according to claim 4, in which the first supplementary piezoelectric means comprises a tubular piezoelectric actuator.

6. A mechanism according to claim 4, in which the first supplementary piezoelectric means comprises a pair of rod-like piezoelectric actuators.

7. A mechanism according to claim 2, in which the second crawler portion includes a second substantially frustoconical recess whose axis is substantially coaxial with the longitudinal axis of the elongate member, and in which the second non-return means comprises a spring loaded collet arranged to seat in the second substantially frustoconical recess to exert a braking action on the second crawler portion, the mechanism further comprising a second supplementary piezoelectric means for moving the collet away from the second substantially frustoconical recess to release the braking action of the second non-return means.

8. A mechanism according to claim 7, in which the second supplementary piezoelectric means comprises a tubular piezoelectric actuator.

9. A mechanism according to claim 7, in which the second supplementary piezoelectric means comprises a pair of rod-like piezoelectric actuators.

10. A mechanism according to claim 2, in which the piezoelectric means is tubular.

11. A mechanism according to claim 10, in which the second crawler portion is held captive on the first crawler portion and is spring biased away therefrom, and in which the piezoelectric means comprises a pair of rod-like piezoelectric actuators.

12. A mechanism according to claim 1, in which the first non-return means and the second non-return means each comprise sprags which brake movement towards the proximal end of the elongate member and which permit movement only in a direction towards the distal end of the elongate member.

13. A mechanism according to claim 1, in which the second crawler portion is held captive on the first crawler portion and is spring biased away therefrom, and in which the piezoelectric means comprises a tubular piezoelectric actuator surrounding the elongate member.

14. A mechanism according to claim 13, in which the first crawler portion comprises a collar having a pair of free ends, the collar being arranged to grip the elongate rod to brake movement of the first crawler portion relative to the elongate rod, and gripping release means comprising a transversely mounted piezoelectric means arranged to separate the free ends of the collar to release the braking action thereof on the elongate member.

15. A mechanism according to claim 13, in which the second crawler portion comprises a collar having a pair of free ends, the collar being arranged to grip the elongate rod to brake movement of the second crawler portion relative to the elongate rod, and gripping release means comprising a transversely mounted piezoelectric means arranged to separate the free ends of the collar to release the braking action thereof on the elongate member.

16. A mechanism according to claim 1, in which the elongate member comprises a tubular portion, in which the first crawler portion comprises a first plug slidably disposed within the tubular portion and connected to an outer ring member which surrounds the elongate member, in which the second crawler portion comprises a second plug slidably disposed within the tubular portion and connected to a main body portion surrounding the elongate member, in which the first non-return means and the second non-return means each comprise respective sprags, in which the piezoelectric drive means is disposed within the tubular portion between the first and second plugs, and in which spring biassing means are provided between the first crawler portion and the second crawler portion and arranged to undergo loading while the first non-return means prevents movement of the first crawler portion during movement of the second crawler portion and for the loading to be released while the second non-return means prevents movement of the second crawler portion so as to cause the first crawler portion to move towards the distal end of the elongate member.

17. A mechanism according to claim 1, in which the control means includes a load sensor for measuring the load applied by or to the piezoelectric drive means.

18. A mechanism according to claim 17, in which the load sensor comprises a load cell.

19. A mechanism according to claim 18, in which the load cell comprises a piezoelectric crystal upon which the piezoelectric drive means is arranged to impinge.

20. A mechanism according to claim 17, in which the control means includes a microprocessor, amplifier means operatively connected to the piezoelectric drive means and under the control of the microprocessor for applying at least one voltage potential signal to the piezoelectric drive means at a selected rate of increase thereof for causing the movable device to move in incremental steps along the elongate member in a controlled manner, feedback amplifier means connected to the load sensor and arranged to receive a feedback signal therefrom, the feedback amplifier means being operatively connected to the microprocessor for supplying thereto a feedback signal in dependence on the load sensed by the load sensor and the microprocessor being arranged to receive the feedback signal from the feedback amplifier means and to adjust the rate of increase of the at least one voltage potential signal so as to ensure that the load exerted by or on the piezoelectric drive means and sensed by the load sensor does not exceed a predetermined value.

21. A mechanism according to claim 20, in which the microprocessor is arranged to store data indicative of the at least one voltage potential signal, of time, and of the feedback signal from the feedback amplifier means.

22. A mechanism according to claim 20, in which the at least one voltage potential signal comprises a d.c. voltage potential signal.

23. A mechanism according to claim 22, in which the at least one voltage potential signal comprises an oscillatory signal with a frequency of from about 5 Hz to about 2 kHz having an amplitude of from about 1 $\mu$m to about 10 $\mu$m imposed upon the d.c. voltage potential signal.

24. A mechanism according to claim 20, in which the microprocessor is connected to an input/output device by means of which set point values can be input into the microprocessor from an external input device and data stored in the microprocessor can be downloaded to an external source.

25. A mechanism according to claim 24, in which the set point values include set point values indicative of at least one of the following items:

(i) the rate of increase of d.c. voltage potential with time applied to the piezoelectric drive means thereby to determine the rate of extension thereof;

(ii) a functional relationship involving the rate of increase of the d.c. voltage potential applied to the piezoelectric drive means and also the load sensed by the load cell;

(iii) the maximum d.c. voltage potential to be applied to the piezoelectric drive means thereby to determine the size of each said incremental step;

(iv) the maximum load sensed by the load sensor permitted to be applied by or to the piezoelectric drive means thereby to determine the load imposed on the bone callus and associated soft tissue;

(iv) the maximum time period during which the movable device is permitted to move thereby to determine the maximum distance through which the movable device is permitted to move along the elongate member;

(v) the maximum distance through which the movable device is permitted to move along the elongate member.

26. A mechanism according to claim 1, in which the incremental steps range from about 5 $\mu$m to about 120 $\mu$m.

27. A mechanism according to claim 26, in which the incremental steps range from about 40 $\mu$m to about 80 $\mu$m.

28. A mechanism according to claim 1, in which the control means is arranged to cause the movable device to move along the movable member at a rate of about 1 mm per day.

29. An auto-extensible tissue distractor fitted with a mechanism according to claim 1.

* * * * *